United States Patent [19]

Hilboll et al.

[11] 4,386,031

[45] May 31, 1983

[54] N-BENZOYL-ω-ANILINO ALKANE CARBOXYLIC ACIDS AND SALTS AND ESTERS THEREOF

[75] Inventors: Gerd Hilboll, Cologne; Hans-Heiner Lautenschläger, Pulheim-Stommeln; Brigitte Stoll, Pulheim; Manfred Probst, Frechen, all of Fed. Rep. of Germany

[73] Assignee: A. Nattermann & Cie GmbH, Cologne, Fed. Rep. of Germany

[21] Appl. No.: 318,964

[22] Filed: Nov. 6, 1981

[30] Foreign Application Priority Data

Nov. 11, 1980 [DE] Fed. Rep. of Germany ....... 3042482

[51] Int. Cl.³ .................... C09F 5/00; C07C 101/453
[52] U.S. Cl. .................... 260/404; 260/404.5; 260/402.5; 560/38; 560/41; 560/9; 560/255; 560/39; 560/108; 562/431; 562/443; 562/444; 562/448; 562/449; 562/450; 424/309; 424/318; 424/319; 549/441
[58] Field of Search ............... 560/38, 39, 9, 41, 255, 560/108, 48; 562/431, 443, 457, 444, 448, 449, 450; 260/404, 404.5 R, 402.5, 340.5 R; 424/309, 318, 319

[56] References Cited

U.S. PATENT DOCUMENTS

| | | | |
|---|---|---|---|
| 2,571,515 | 10/1951 | Archer | 200/404.5 R |
| 3,732,295 | 5/1973 | Dompe | 562/444 |
| 3,769,334 | 10/1973 | Garzia | 560/39 |
| 3,769,335 | 10/1973 | Garzia | 260/404 |
| 4,243,678 | 1/1981 | Krastinat | 562/457 |
| 4,250,183 | 2/1981 | Krastinat | 562/450 |

FOREIGN PATENT DOCUMENTS

1917036  1/1971  Fed. Rep. of Germany ...... 562/445

OTHER PUBLICATIONS

Evans et al., J. Med. Chem., vol. 12, pp. 1006–1010 (1969).

Primary Examiner—James H. Reamer
Attorney, Agent, or Firm—Pearne, Gordon, Sessions, McCoy, Granger & Tilberry

[57] ABSTRACT

The present invention refers to N-Benzoyl-ω-anilinoalkane carboxylic acids, their esters and salts of the general formula

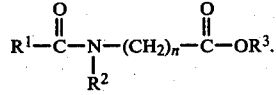

18 Claims, No Drawings

N-BENZOYL-ω-ANILINO ALKANE CARBOXYLIC ACIDS AND SALTS AND ESTERS THEREOF

The present invention refers to new N-Benzoyl-ω-anilino-$C_{7-10}$-alkano carboxylic acids, their pharmaceutically compatible salts and $C_{1-7}$-alkylesters, process for producing these compounds and pharmaceutical preparations containing the same.

N-Benzoyl-ω-anilino-$C_7$-$C_6$-alkano carboxylic acids already have been tested several times for their pharmacological activity (D. Evans et al., M. Med. Chem. 12 (1969) pgs. 1006 to 1010; German Offenlegungsschrift No. 19 17 036). The compounds partly showed choleretic activity. However, the tests further showed that such compounds do not have an antiinflammatory activity.

Surprisingly, the new N-benzoyl-ω-anilino-$C_{7-10}$-alkano carboxylic acids, their alkali salts and esters show pharmacological properties which have not been expected namely antiallergic, thrombocyte aggregation inhibitory, antiinflammatory and lipide lowering activity. Since the new compounds furthermore show a low toxicity and a good compatibility, they are in particular useful for the treatment of allergic, asthmatic, thromboembolic, inflammatory and arteriosclerotic diseases. The new compounds may also be preferably combined with other active agents such as anticoagulantia, in particular heparine, heparinates and coumarine derivatives. In particular, in the prophylaxis of thromboembolic complications it is desirable to influence the thrombocyte aggregation and the coagulation of the blood. In this respect, the compounds of the present application show particular activity in combination with anticoagulantia, in particular with heparine and heparinates.

Thus, object of the present invention are the new N-benzoyl-ω-anilino alkane carboxylic acids and their derivatives of the general formula I

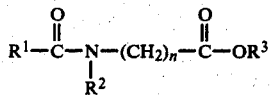

wherein n is a positive integer ranging from 7 to 10, $R^1$ and $R^2$, which may be identical or different from each other, represent the unsubstituted phenyl group or the phenyl groups substituted by 1 to 4 equal or different radicals selected from the group of halogen, in particular chlorine or fluorine; $C_{1-4}$-alkyl, in particular methyl; $C_{1-4}$-alkoxy, in particular methoxy or ethoxy; $C_{1-4}$-alkylthio, in particular methylmercapto or ethylmercapto; acyloxy, in particular $C_{1-4}$-alkanacyl, most preferably acetoxy, propionyloxy or benzoyloxy; halo-$C_{1-4}$-alkyl, in particular trifluoromethyl; hydroxy; phenoxy; benzyloxy; di-$C_{1-4}$-alkylamino, in particular dimethylamino;

$R^3$ is hydrogen, an alkali metal ion, in particular the sodium metal ion, or a straight or branched saturated hydrocarbon group having from 1 to 7 carbon atoms such as and in particular ethyl, isopropyl or heptyl; or the benzyl group.

Preferred substituted phenyl groups $R^1$ are: 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-(trifluoromethyl)-phenyl, 3-(trifluoromethyl)-phenyl, 2-hydroxyphenyl, 3-hydroxyphenyl, 4-hydroxyphenyl, 2-acetoxyphenyl, 3-acetoxyphenyl, 4-acetoxyphenyl, 2-methoxyphenyl, 3-methoxyphenyl, 4-methoxyphenyl, 2-benzyloxyphenyl, 3-benzyloxyphenyl, 4-benzyloxyphenyl, 2-phenoxyphenyl, 3-phenoxyphenyl, 2-methylmercaptophenyl, 4-methylmercaptophenyl, 3-(dimethylamino)-phenyl, 4-(dimethylamino)-phenyl, 2.6-difluorophenyl, 2.4-dichlorophenyl, 2.5-dichlorophenyl, 2.6-dichlorophenyl, 3.4-dichlorophenyl, 3.5-dichlorophenyl, 2.3-dimethylphenyl, 2.4-dimethylphenyl, 2.5-dimethylphenyl, 2.6-dimethylphenyl, 3.4-dimethylphenyl, 3.5-dimethylphenyl, 2.3-dihydroxyphenyl, 2.4-dihydroxyphenyl, 2.5-dihydroxyphenyl, 2.6-dihydroxyphenyl, 3.4-dihydroxyphenyl, 3.5-dihydroxyphenyl, 2.3-dimethoxyphenyl, 2.4-dimethoxyphenyl, 2.6-dimethoxyphenyl, 3.4-dimethoxyphenyl, 3.5-dimethoxyphenyl, 3.4-methylendioxyphenyl, 2.4.6-trimethylphenyl, 2.3.4-trimethoxyphenyl, 2.4.5-trimethoxyphenyl, 3.4.5-trimethoxyphenyl, 3-fluoro-4-methylphenyl, 5-fluoro-2-hydroxyphenyl, 2-chloro-6-fluorophenyl, 3-chloro-4-hydroxyphenyl, 4-chloro-2-hydroxyphenyl, 5-chloro-2-hydroxyphenyl, 4-chloro-2-methoxyphenyl, 5-chloro-2-methoxyphenyl, 4-dimethylamino-2-hydroxyphenyl, 2-hydroxy-4-methoxyphenyl, 2-hydroxy-3-methoxyphenyl, 2-hydroxy-5-methoxyphenyl, 4-hydroxy-3-methoxyphenyl, 2-hydroxy-3-methylphenyl, 3-hydroxy-4-methylphenyl, 3-methoxy-4-methylphenyl, 3.5-dichloro-4-hydroxyphenyl, 3.5-dimethoxy-4-hydroxyphenyl.

Preferred substituted phenyl groups $R^2$ are: 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-(trifluoromethyl)-phenyl, 3-(trifluoromethyl)-phenyl, 4-(trifluoromethyl)-phenyl, 2-hydroxyphenyl, 3-hydroxyphenyl, 4-hydroxyphenyl, 2-methoxyphenyl, 3-methoxyphenyl, 4-methoxyphenyl, 3-benzyloxyphenyl, 4-benzyloxyphenyl, 4-phenoxyphenyl, 2-methylmercaptophenyl, 3-methylmercaptophenyl, 4-(dimethylamino)-phenyl, 2.4-difluorophenyl, 2.6-difluorophenyl, 2.3-dichlorophenyl, 2.4-dichlorophenyl, 2.5-dichlorophenyl, 2.6-dichlorophenyl, 3.4-dichlorophenyl, 3.5-dichlorophenyl, 2.3-dimethylphenyl, 2.4-dimethylphenyl, 2.5-dimethylphenyl, 2.6-dimethylphenyl, 3.4-dimethylphenyl, 3.5-dimethylphenyl, 2.4-dimethoxyphenyl, 2.5-dimethoxyphenyl, 3.4-dimethoxyphenyl, 3.5-dimethoxyphenyl, 3.4-methylendioxyphenyl, 2.4.6-trimethylphenyl, 3.4.5-trimethoxyphenyl, 5-fluoro-2-methylphenyl, 5-chloro-2-hydroxyphenyl, 2-chloro-4-methylphenyl, 2-chloro-6-methylphenyl, 3-chloro-2-methylphenyl, 3-chloro-4-methylphenyl, 4-chloro-2-methylphenyl, 5-chloro-2-methylphenyl, 2-chloro-5-methoxyphenyl, 2-chloro-5-(trifluoromethyl)-phenyl, 4-chloro-3-(trifluoromethyl)-phenyl, 2-hydroxy-4-methylphenyl, 2-hydroxy-5-methylphenyl, 4-hydroxy-2-methylphenyl, 2-methoxy-5-methylphenyl, 4-methoxy-2-methylphenyl, 5-methoxy-3-(trifluoromethyl)-phenyl, 5-chloro-2.4-dimethoxyphenyl, 3.5-dichloro-4-hydroxyphenyl.

Subject matter of the present invention is furthermore a process for producing the compounds of the general formula I which is characterized in that a benzanilide of formula II

wherein $R^1$ and $R^2$ have the same meaning as in formula I is subjected to reaction with an alkylating agent of formula III

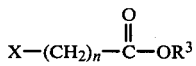

wherein n has the same meaning as in formula I, $R^3$ is a $C_{1-7}$-alkyl group and X is a halogen atom such as a chlorine, bromine or iodine atom, in an organic solvent such as acetone, methylethylketone, dimethylformamide, with the addition of a basic compound such as sodium hydride and possibly in the presence of an alkali metal iodide as catalyst.

The benzanilide of formula II may readily be obtainable in known manners by acylation of an aniline derivative of the formula IV $$R^2\text{---}NH_2 \qquad\qquad IV$$

with a reactive benzoic acid derivative of formula V

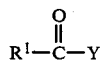

such as an acid halogenide, acid anhydride, acid imidazolide or a reactive ester.

The esters of formula I possibly are hydrolysed at room temperature in usual manners by reaction with an alkali hydroxide in aqueous, alcoholic or alcoholic-etheric solvents to yield an alkali salt of formula I ($R^3$=alkali metal) with subsequent addition of a mineral acid to yield an acid of formula I ($R^3$=H).

The esters of formula I may also be produced in that an aniline derivative of formula III is subjected to reaction with an alkylating agent of formula IV in a suitable organic solvent such as benzene, toluene, cyclohexane, dimethylformamide, possibly with the addition of a tertiary amine such as triethylamine, ethyldiisopropylamine, possibly in the presence of an alkali metal iodide as catalyst, and subjecting the resulting ω-anilinoalkane carboxylic acid esters of formula VI

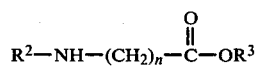

wherein $R^2$, $R^3$ and n have the same meaning as in formula I, in a suitable organic solvent such as benzene, toluene, diethylether, tetrahydrofurane, dioxane, possibly in the presence of a tertiary amine such as triethylamine, ethyldiisopropylamine, pyridine, to reaction with a reactive benzoic acid derivative of formula V.

The acides of formula I ($R^3$=H) may also be produced in that an ω-anilinoalkane carboxylic acid esters of formula VI ($R^3$=alkyl) is saponified in usual manners to yield an ω-anilinoalkane carboxylic acid of formula VI ($R^3$=H) and acylating the same in an aqueous or aqueous ethereal solvent in the presence of an alkali metal hydroxide with a benzoic acid halogenide.

Finally, the esters of formula I ($R^3$=alkyl) having at least one free phenolic hydroxy group may be produce in that a compound of formula I ($R^3$=H, alkyl) wherein at least one $R^1$ and $R^2$ represents a benzyloxy substituted phenyl group of formula VII

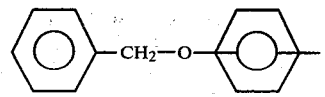

is subjected to reaction with hydrogen in the presence of a suitable catalyst such as Raney-nickel, platinumoxide, palladium, in a suitable solvent such as anhydrous methanol or ethanol.

If desired, the acids of formula I ($R^3$=H) may be reacted with an alkali metal hydroxide or carbonate in usual manners to yield the alkali metal salts of formula I ($R^3$=alkali metal) or, respectively, with an acid or alkali salt of the formula I ($R^3$=H, alkali metal) may be reacted in a suitable solvent such as dimethylformamide, possibly in the presence of an alkali metal carbonate, with an alkylating agent of formula VIII $$Z\text{---}R^3 \qquad\qquad VIII$$

wherein Z is a halogen such as chlorine, bromine, iodine or another suitable group to be split off and $R^3$ is a straight or branched $C_{1-7}$-alkyl group or an aralkyl group to yield the corresponding esters.

Starting materials of formula II are for instance the benzanilides, $R^1$ and $R^2$ having the same meaning as in formula I. Starting materials of formula III are for instance the esters of the following ω-halogenoalkane carboxylic acids: 8-chlorocaprylic acid, 8-bromocaprylic acid, 8-iodocaprylic acid, 9-chloropelargonic acid, 9-bromopelargonic acid, 9-iodepelargonic acid, 10-chlorocaprinic acid, 10-bromocaprinic acid, 10-iodocaprinic acid, 11-chloroundecanic acid, 11-bromoundecanic acid, 11-iodoundecanic acid.

Starting materials of formula IV are for instance the aniline derivatives, $R^2$ having the same meaning as in formula I. Starting materials of formula V are for instance suitable derivatives such as acid halogenides, acid anhydrides, acid imidazolides, reactive esters of benzoic acid, $R^1$ having the same meaning as in formula I.

Alkylating agents of formula VIII are for instance: Iodomethane, bromoethane, iodoethane, 1-chloropropane, 1-iodopropane, 2-chloropropane, 2-bromopropane, 1-chlorobutane, 1-bromobutane, 2-bromo-2-methylpropane, 2-chlorobutane, 2-bromobutane, 1-chloropentane, 2-bromopentane, 1-bromo-2-methylbutane, 1-chlorohexane, 1-bromohexane, 1-chloroheptane, 1-bromoheptane, benzylchloride, benzylbromide, 2-chlorobenzylchloride, 4-chlorobenzylchloride, 4-fluorobenzylchloride, 4-(trifluoromethyl)-benzylchloride, 4-methoxybenzylchloride, 3.4.5-trimethoxybenzylchloride, 1-chloro-2-phenylethane, 1-chloro-1-phenylethane, 3-chloro-1-phenylpropane, 2-chloro-1-phenylpropane, 4-chloro-1-phenylbutane, dimethylsulfate, p-toluene sulfonic acid ethyl ester.

Subject matter of the present invention are pharmaceutical preparations containing one or several of the new compounds of formula I besides non-toxic, inert pharmaceutical suitable carrier materials and processes for producing the same.

Subject matter of the present invention are furthermore suitable preparations in dosage form such as tablets, dragees, capsules, pills, suppositories and ampoules containing the active agent in fraction or in a multitude of a single dose. The dosage unit forms may contain 1, 2, 3 or 4 single dosages or ½, ⅓ or ¼ of a single dosage.

The single dosage preferably contains such amount of the active agent which is administered during application and in general corresponds to a daily dose, half a daily dose, or one third or one quarter of a daily dose.

Non-toxic inert, pharmaceutically useful carrier materials are solid, semi-solid or liquid diluents, fillers and additives of any known kind. Preferred pharmaceutical preparations are tablets, dragees, capsules, pills, granulates, suppositories, solutions, suspensions and emulsions, pastes, ointments, gels, lotions, powders and sprays.

Tablets, dragees, capsules, pills and granulates may contain one or several active agents according to the present invention besides usual carrier material such as fillers and diluents (for instance starch products, lactose, sucrose, glucose, mannitol and silicic acid), binders (for instance carboxymethyl cellulose, alginates, gelatine, polyvinylpyrrolidone), humidifiers (for instance glycerol), desintegrants (for instance agar-agar, calcium carbonate and sodium carbonate), anti-soluents (for instance paraffine) and resorption increasing agents (for instance quaternary ammonium compounds), adsorbents (for instance kaoline and bentonite) and lubricants (for instance talcum, calcium stearate and magnesium stearate and solid polyethylene glycoles) or mixtures of the above compounds.

The tablets, dragees, capsules, pills and granulates may comprise the usual covers which may contain agents for rendering them opaque, and may be so constructed in usual manners that they deliberate the active agent or agents only or only partly or retarded the embedding materials, for instance being polymeric products and waxes.

The active agent or agents may possibly also be present in microcapsules in order to obtain a retarding effect.

Suppositories may contain in addition to the active agent or agents usual carrier materials soluble or insoluble in water such as polyethylene glycoles, fats such as cacao butter fat or higher esters such as $C_{14}$-alcohol with $C_{16}$-fatty acid; or mixtures of the above.

Ointments, pastes, cremes and gels may beside the active agent or agents contain usual carrier materials for instance fats of animal or plant origin, waxes, paraffines, starches, tragant or mixtures of the above products.

Powders and sprays besides the active agent or agents may contain usual carrier materials such as lactose, talcum, silicic acid, aluminum hydroxide or mixtures of the above compounds. Sprays furthermore may contain usual propellants.

Solutions or emulsions beside the active agent or agents may contain usual carrier materials such as solvents, solubilizers and emulgators, for instance water, ethyl-alcohol, isopropyl alcohol, ethyl carbonate, ethyl acetate, benzyl alcohol, benzyl benzoate, propylene glycol, oils, in particular cotton seed oil, peanut oil, corn seedling oil, olive oil and sesame oil, glycerol, polyethylene glycols or mixtures of the above compounds.

For parenteral application, the solutions and emulsions may be sterilized and may be in blood isotonic form.

Suspensions beside the active agent or agents may contain usual carrier materials such as liquid diluents for instance water, ethyl alcohol, propylene glycol, emulgators such as ethoxylated isostearyl alcohol, polyoxyethylene sorbitol and polyoxyethylene sorbitolesters, microcrystalline cellulose or mixtures of the above compounds.

The above products may also contain coloring agents, as well as additives improving the smell and taste thereof such as peppermint oil and eucalyptus oil as well as sweeteners for instance saccharine.

The therapeutic active agents are present in the above pharmaceutical preparations in amounts ranging from about 0.1 to about 99.5, preferably from about 0.5 to about 95% of the weight of the total mix.

Besides the active agent or agents according to the present invention, the above pharmaceutical preparations may further contain other pharmaceutical active agents such as heparine, heparinates or coumarine derivatives.

The production of the above pharmaceutical preparations occurs in usual manners by usual methods for instance by mixing of the active agent or agents with the carrier material or materials.

A further part of the present invention is the use of the above new active agents of formula I as well as the pharmaceutical preparations containing one or several active agents according to the present invention in the human and veterinary medicine in the treatment of thromboembolic, inflammatory and arteriosclerotic processes in the human and in animal organisms.

The active agents or the pharmaceutical preparations may be administered locally, orally, parenterally, intraperitoneally and/or rectally, preferably orally and/or parenterally.

In general it is preferred in human medicine to use the active agent or agents in a total amount of about 10 to 2,000, preferably 30 to 500 mg per each 24 hours, possibly in the form of several single dosages in order to obtain best results. Each single dosage contains the active agent, preferably in amounts of about 10 to about 300, in particular 50 to 200 mg per dosage.

However, if necessary the above dosages may be increased and this depending upon the kind and the body weight of the being to be treated, the kind and severeness of the illness, the kind of preparation and application of the active agent and the interval at which single dosages are applied. For instance it may be sufficient in some cases to use less amounts of the active agent as above indicated while in other cases the above amounts may have to be increased. The single dose to be applied for obtaining optimal results may be determined by the doctor according to his general knowledge.

The preparation of the compounds according to the present invention is further illustrate in the following examples.

The reactive benzoic acid derivatives according to formula V and the benzanilides according to formula II are known compounds and may be produced according to known processes (L. GATTERMANN and H. WIELAND, Die Praxis des organischen Chemikers, 35. Auflage, p. 112; W. DE GRUYTER ET AL., Berlin 1953; H. FRANZEN, Ber.dtsch.chem.Ges. 42, (1909) p. 2465).

The recited melting points have been determined in a Büchi 510 apparatus and are not corrected. The IR spectra have been determined on a Perkin-Elmer 257 and the mass spectra on a Varian MAT-311A (70 eV).

EXAMPLE 1

8-(N-Phenyl-benzamido)-caprylic acid

R$^1$=phenyl, R$^2$=phenyl, n=7, R$^3$=H (a) 8-(N-Phenyl-benzamido)-caprylic acid methyl ester 2.4 g (0.1 mol) of sodium hydride are added to a solution of 19.7 g (0.1 mol) of benzanilide in 200 cc. of dimethylformamide. The mixture is stirred at about 40° C. until termination of hydrogen formation.

Thereafter, 23.7 g (0.1 mol) of 8-bromocaprylic acid methyl ester and 3 g (0.02 mol) of sodium iodide are added and the mixture is stirred at 90° C. for 6 hours. After cooling, the majority of the solvent is distilled off in a vacuum and the residue is poured into about 300 cc. of water. The separated crude product is dissolved in chloroform, the chloroform layer is washed with 5% sulfuric acid, with water, with 5% bicarbonate solution and finally again with water. The organic layer is dried over Na$_2$SO$_4$ and the solvent is distilled off in a vacuum. The crude product is used in the next step without any further purification.

Yield: 28.2 g (80%) of a read oil.
IR (film): 1740 and 1646 cm$^{-1}$.

(b) 8-(N-Phenyl-benzamido)-caprylic acid 21.7 g (0.06 mol) of 8-(N-phenyl-benzamido)-caprylic acid methylester are dissolved in 80 cc. of methanol. 3.9 g (0.07 mol) of potassium hydroxide are added thereto. The mixture is stirred at 25° C. for 48 hours, the solvent is distilled off and the residue is dissolved in water. The aqueous phase is several times shaken with ether, the ethereal layers are discarded. The aqueous phase is acidified with dilute hydrochloric acid and is extracted with ether. The ethereal layer is washed with water and dried over MgSO$_4$. The solvent is distilled off and the residue is purified chromatographically on silicic acid using a mixture of chloroform and methanol as eluant.

Yield: 4.7 g (23% of the theoretical), Fp. 58°–60° C.
IR (in KBr): 1710 and 1645 cm$^{-1}$.
MS (m/e): 339 (17%), 197 (39%), 105 (100%), 77 (20%).

EXAMPLE 2

8-[4-Chloro-N-(4-chlorophenyl)-benzamido]-caprylic acid

R$^1$=4Chlorophenyl, R$^2$=4-Chlorophenyl, n=7, R$^3$=H (a) 8-[4-Chloro-N-(4-chlorophenyl)-benzamido]-caprylic acid methyl ester As described in example 1(a), 2.4 g (0.1 mol) of sodium hydride, 25.2 g (0.1 mol) of 4-chloro-N-(4-chlorophenyl)-benzamid, 200 ml dimethylformamide, 23.7 g (0.1 mol) of 8-bromocaprylic acid methyl ester and 3 g (0.02 mol) of sodium iodide are reacted. Reaction time: 5.5 hours; reaction temperature: 110° C. The crude product is used in the next step without any further purification.

Yield: 40 g (95% of the theoretical) of a read oil.

(b) 8-[4-Chloro-N-(4-chlorophenyl)-benzamido]-caprylic acid

As described in example 1(b), the reaction is carried out with 40 g of 8-[4-chloro-N-(4-chlorophenyl)-benzamido]-caprylic acid methyl ester, 150 ml of methanol and 4 g (0.1 mol) of sodium hydroxide. Reaction time: 4 hours; reaction temperature: 25° C. The purification of the resulting crude product occurs chromatographically on silicic acid using a mixture of chloroform and methanol as eluant.

Yield: 8.9 g (23% of the theoretical) Fp. 94°–95° C. (from ethyl acetate).
IR (in KBr): 1720 and 1640 cm$^{-1}$.
MS(m/e): 407 (15%), 265 (23%), 139 (100%), 111 (14%).

EXAMPLE 3

8-[4-Methoxy-N-(4-methoxyphenyl)-benzamido]-caprylic acid

R$^1$=4-Methoxyphenyl, R$^2$=Methoxyphenyl, n=7, R$^3$=H (a) 8-(4-Methoxyphenylamino)-caprylic acid methyl ester A mixture of 19.7 g (0.16 mol) of p-anisidine, 37.9 g (0.16 mol) of 8-bromocaprylic acid methyl ester, 16.2 g (0.16 mol) of triethylamine and 120 ml of cyclohexane are stirred with boiling for 3 hours. The precipitated triethylamine-hydrobromide is filtered off from the hot mixture, the solvent is distilled off from the filtrate, and residue is recrystallized from cyclohexane.

Yield: 21.3 g (48% of the theoretical) Fp. 72°–73° C. (from cyclohexane).
IR (in KBr): 3400 and 1735 cm$^{-1}$.
MS (m/e): 279 (51%), 248 (7%), 136 (100%), 108 (3%).

(b) 8-[4-Methoxy-N-(4-methoxyphenyl)-benzamido]-caprylic acid methyl ester 12 g (43 mmol) of 8-(4-methoxyphenylamino)-caprylic acid methyl ester are dissolved in 400 cc. of ether. 5.1 g (50 mmol) of triethylamine are added thereto. 7.3 g (43 mmol) of 4-methoxybenzoic acid chloride are added dropwise to the mixture with stirring and cooling with ice. After the addition, stirring is continued at 25° C. for 5 hours. The separated triethylamine-hydrochloride is filtered off with suction and the ethereal phase is washed in sequence with water, 5% bicarbonate solution, water, 2 n hydrochloric acid and water is dried over Na$_2$SO$_4$, and the solvent is distilled off. The crude product is used in the next step without any further purification.

Yield: 15.8 g (89% of the theoretical) of a colourless oil.

(c) 8-[4-Methoxy-N-(4-methoxyphenyl)-benzamido]-caprylic acid

As described in example 1(b), 10 g (24 mmol) of 8-[4-methoxy-N-(4-methoxyphenyl)-benzamido]-caprylic acid methyl ester is reacted with 2 g (50 mmol) of sodium hydroxide and 200 cc. of methanol. Reaction time: 6 hours, reaction temperature: 25° C.

Yield: 8.8 g (92% of the theoretical) of a colourless oil.
IR (film): 1735, 1710, 1640, 1615 cm$^{-1}$.
MS (m/e): 399 (35%), 257 (5%), 135 (100%), 107 (3%).

EXAMPLE 4

8-[4-Chloro-N-(4-methoxyphenyl)-benzamido]-caprylic acid $R^1$=4-Chlorophenyl, $R^2$=4-Methoxyphenyl, n=7, $R^3$=H (a)

8-[4-Chloro-N-(4-methoxyphenyl)-benzamido]-caprylic acid methyl ester

As described in example 1(a), the reaction is carried out with 130.7 g (0.5 mol) of 4-chloro-N-(4-methoxyphenyl)-benzamide, 24.5 g (1 mol) sodium hydride, 700 cc. of dimethylformamide and 118.5 g (0.5 mol) of 8-bromocaprylic acid methyl ester. Reaction time and reaction temperature: 5 hours at 80° C., thereafter 12 hours at 100° C. The reaction mixtures are further processed as described in example 1(a). The crude product is dissolved in 300 cc. of ether. After standing for a prolonged period, the unreacted 4-chloro-N-(4-methoxyphenyl)-benzamide separates by crystallisation and is filtered off. The solvent is partly distilled off and the resulting oily crude product (181 g) is separated. 125 g are used in the next step without further purification, the remainder (56 g) is purified chromatographically on silicic acid using chloroform as eluant.

Yield: 19 g (30% of the theoretical) of a colourless oil.
IR (film): 1742 and 1647 cm$^{-1}$.
MS (m/e): 417 (40%), 261 (29%), 139 (100%), 136 (10%), 125 (9%).

(b)

8-[4-Chloro-N-(4-methoxyphenyl)-benzamido]-caprylic acid

As described in example 1(b), the reaction is carried out with 125 g (0.3 mol) of 8-[4-chloro-N-(4-methoxyphenyl)-benzamido]-caprylic acid methyl ester, 500 cc. of methanol and 12 g (0.3 mol) of sodium hydroxide. Reaction time: 2 days, reaction temperature: 25° C. 40 g of the crude product (96.3 g) are purified chromatographically on silicic acid using a mixture of chloroform and methanol (99:1) as eluant.

Yield: 32.8 g (67% of the theoretical) of a colourless oil.
IR (film): 1735, 1715, 1645, 1625 cm$^{-1}$.
MS (m/e): 403 (65%), 261 (17%), 139 (100%), 136 (17%), 111 (11%).

EXAMPLE 5

9-[4-Chloro-N-(4-methoxyphenyl)-benzamido]-pelargonic acid $R^1$=4-Chlorophenyl, $R^2$=4-Methoxyphenyl, n=8, $R^3$=H (a) 9-(4-Methoxyphenylamino)-pelargonic acid methyl ester As described in example 3(a), the reaction is carried out with 6.2 g (0.05 mol) of p-anisidine, 5.1 g (0.05 mol) of triethylamine, 12.6 g (0.05 mol) of 9-bromopelargonic acid methyl ester and 40 cc. of cyclohexane.

Yield: 2.3 g (15% of the theoretical) Fp. 50°–52° C. (from ethanol).
IR (in KBr): 3400 and 1735 cm$^{-1}$.
MS (m/e): 293 (29%), 262 (4%), 136 (100%).

(b) 9-[4-Chloro-N-(4-methoxyphenyl)-benzamido]-pelargonic acid methyl ester

As described in example 3(b) the reaction is carried out with 2 g. (6.8 mmol) of 9-(4-methoxyphenylamino)-pelargonic acid methyl ester, 0.75 g (7.5 mmol) of triethylamine, 1.2 g (6.8 mmol) of 4-chlorobenzoic acid chloride and 80 cc. of ether. The crude product is used in the next reaction step without further purification.

Yield: 2.8 g (95% of the theoretical) of a colourless oil.

(c)

9-[4-Chloro-N-(4-methoxyphenyl)-benzamido]pelargonic acid

As described in example 1(b), the reaction is carried out with 2.8 g (6.5 mmol) of 9-[4-chloro-N-(4-methoxyphenyl)-benzamido]-pelargonic acid methyl ester, 0.3 g (7.8 mmol) of sodium hydroxide and 50 cc. of methanol. Reaction time: 42 hours, reaction temperature: 25° C.

Yield: 2 g (74% of the theoretical) of a colourless oil.
IR (film): 1732, 1710, 1640 and 1618 cm$^{-1}$.
MS (m/e): 417 (45%), 261 (31%), 139 (100%), 136 (17%), 111 (10%).

EXAMPLE 6

11-[4-Chloro-N-(4-methoxyphenyl)-benzamido]-undecanoic acid $R^1$=4-Chlorophenyl, $R^2$=4-Methoxyphenyl, n=10, $R^3$=H (a)

11-[4-Chloro-N-(4-methoxyphenyl)-benzamido]-undecanoic acid methyl ester

As described in example 1(a), the reaction is carried out with 28.7 g (0.11 mol) of 4-chloro-N-(4-methoxyphenyl)-benzamide, 4.5 g (0.18 mol) of sodium hydride, 36.7 g (0.13 mol) of 11-bromoundecanoic acid methyl ester, 100 cc. of dimethylformamide and 3 g (0.02 mol) of sodium iodide. Reaction time: 5 hours, reaction temperature: 80° C. The crude product is used in the next step without further purification.

Yield: 31.2 g (62% of the theoretical) of a brownish oil.

(b)

11-[4-Chloro-N-(4-methoxyphenyl)-benzamido]-undecanoic acid

As described in example 1(b), the reaction is carried out with 31.2 g (68 mmol) of 11-[4-chloro-N-(4-methoxyphenyl)-benzamido]-undecanoic acid methyl ester, 4.4 g (0.11 mol) of sodium hydroxide and 200 cc. of methanol. Reaction time: 15 hours, reaction temperature: 25° C. The crude product is further purified chromatographically on silicic acid gel using chloroform as eluant.

Yield: 3.2 g (11% of the theoretical) of a colourless oil.
IR (film): 1730, 1711, 1642, 1620 cm$^{-1}$.
MS (m/e): 445 (79%), 261 (20%), 139 (100%), 136 (19%), 111 (6%).

EXAMPLE 7

8-[4-Fluoro-N-(4-methoxyphenyl)-benzamido]-caprylic acid $R^1$=4-Fluorophenyl, $R^2$=4-Methoxyphenyl, n=7, $R^3$=H (a)

8-[4-Fluoro-N-(4-methoxyphenyl)-benzamido]-caprylic acid methyl ester

As described in example 3(b), the reaction is carried out with 5.6 g (20 mmol) of 8-(4-methoxyphenylamino)-caprylic acid methyl ester, 5 g (50 mmol) of triethylamine, 150 cc. of toluene and 4 g (25 mmol) of 4-fluorobenzoic acid chloride. Reaction time: 5 hours, reaction temperature: 25° C. The crude product is used in the next reaction step without further purification.

Yield: 7.4 g (92% of the theoretical) of a colourless oil.

(b)

8-[4-Fluoro-N-(4-methoxyphenyl)-benzamido]-caprylic acid

As described in example 1(b), the reaction is carried out with 7.4 g (18 mmol) of 8-[4-fluoro-N-(4-methoxyphenyl)-benzamido]-caprylic acid methyl ester, 1.4 g (35 mmol) of sodium hydroxide and 70 cc. of methanol. Reaction time: 10 hours, reaction temperature: 25° C. The crude product is further purified chromatographically on silicic acid gel using chloroform as eluant.

Yield: 5.2 g (73% of the theoretical) of a colourless oil.

IR (film): 1730, 1710, 1645, 1630 $cm^{-1}$.

MS (m/e): 387 (52%), 264 (14%), 245 (29%), 136 (13%), 123 (100%).

EXAMPLE 8

8-[3-Trifluoromethyl-N-(4-methoxyphenyl)-benzamido]-caprylic acid $R^1$=3-(Trifluoromethyl)-phenyl, $R^2$=4-Methoxyphenyl, n=7, $R^3$=H (a) 8-(4-Methoxyphenylamino)-caprylic acid As described in example 1(b), the reaction is carried out with 10 g (36 mmol) of 8-(4-methoxyphenylamino)-caprylic acid methyl ester, 1.43 g (36 mmol) of sodium hydride and 200 cc. of methanol. Reaction time: 24 hours, reaction temperature: 25° C.

Yield: 8.3 g (87% of the theoretical) Fp. 94°–95° C. (from ether).

IR (in KBr): 3370 and 1713 $cm^{-1}$.

MS (m/e): 265 (29%), 136 (100%), 108 (4%).

(b)

8-[3-Trifluoromethyl-N-(4-methoxyphenyl)-benzamido]-caprylic acid 6.1 g (23 mmol) of 8-(4-Methoxyphenylamino)-caprylic acid are dissolved in 40 cc. of 0.2 n soda lye. A solution of 4.4 g (23 mmol) of 3-(Trifluoromethyl)-benzoic acid fluoride in 50 cc. of ether are added thereto within 20 minutes with vivid stirring dropwise at 25° C., holding the pH at between 7.2 and 8 by the dropwise addition of 0.2 n soda lye. After the addition, vivid stirring is continued for 30 minutes. The mixture is then acidified to pH 3 by the addition of 2 n hydrochloric acid. The aqueous and ethereal layers are separated. The aqueous phase is extracted several times with ether and then is rendered alkaline by the addition of calcium hydroxide. The separated calcium fluoride is filtered off with suction and is discarded. The purified ethereal phase is shaken with water, dried over $MgSO_4$ and the solvent is distilled off. The residue is purified chromatographically on silicic acid gel using chloroform as eluant.

Yield: 0.65 g (6.5% of the theoretical) of a colourless oil.

IR (film): 1738, 1715, 1648, 1625 $cm^{-1}$.

MS (m/e): 437 (45%), 295 (36%), 173 (100%), 145 (19%), 136 (18%), 125 (19%).

EXAMPLE 9

8-[2.4-Dichloro-N-(4-methoxyphenyl)-benzamido]-caprylic acid $R^1$=2.4-Dichlorophenyl, $R^2$=4-Methoxyphenyl, n=7, $R^3$=H (a)

8-[2.4-Dichloro-N-(4-methoxyphenyl)-benzamido]-caprylic acid methyl ester

As described in example 1(a), the reaction is carried out with 32.8 g (0.1 mol) of 2.4-dichloro-N-(4-methoxyphenyl)-benzamide [produced by acylation of p-anisidine with 2.4-dichlorobenzoic acid chloride in toluene in the presence of triethylamine, Fp. 164° C. (from ethanol)], 2.4 g (0.1 mol) of sodium hydride, 200 cc. of dimethylformamide, 23.7 g (0.1 mol) of 8-bromocaprylic acid methyl ester and 6 g (0.04 mol) of sodium iodide. Reaction time: 2.5 hours, reaction temperature: 110°–120° C. The crude product is used in the next reaction step without further purification.

Yield: about 35 g (77% of the theoretical) of a brownish oil.

(b)

8-[2.4-Dichloro-N-(4-methoxyphenyl)-benzamido]-caprylic acid

As described in example 1(b), the reaction is carried out with 35 g (77 mmol), of 8-[2.4-dichloro-N-(4-methoxyphenyl)-benzamido]-caprylic acid methyl ester, 4 g (0.1 mol) of sodium hydroxide, 150 cc. of methanol and 5 cc. of water. Reaction time: 24 hours, reaction temperature: 25° C. The crude product is further purified chromatographically on silicic acid gel using a mixture of n-hexane and ethyl acetate (2:1) as eluant.

Yield: 20.5 g (61% of the theoretical). Fp. 67° C.

IR (in KBr): 1735, 1712, 1652, 1625 $cm^{-1}$.

MS (m/e): 437 (55%), 314 (9%), 295 (51%), 173 (100%), 136 (21%), 125 (19%).

EXAMPLE 10

8-[4-Chloro-N-(2.6-dimethylphenyl)-benzamido]-caprylic acid $R^1$=4-Chlorophenyl, $R^2$=2.6-Dimethylphenyl, n=7, $R^3$=H (a)

8-[4-Chloro-N-(2.6-dimethylphenyl)-benzamido]-caprylic acid methyl ester

As described in example 1(a), the reaction is carried out with 11 g (42 mmol) of 4-chloro-N-(2.6-dimethylphenyl)-benzamide, 1.8 g (75 mmol) of sodium hydroxide, 12 g (50 mmol) of 8-bromocaprylic acid methyl ester, 100 cc. of dimethylformamide and 1.2 g (8 mmol) of sodium iodide. Reaction time: 4 hours, reaction temperature: 110°-120° C. The crude product is used in the next reaction step without further purification.

Yield: 15.8 g (90% of the theoretical) of a read oil.
IR (film): 1745 and 1645 cm$^{-1}$.

(b) 8-[4-Chloro-N-(2.6-dimethylphenyl)-benzamido]-caprylic acid

As described in example 1(b), the reaction is carried out with 15.8 g (38 mmol) of 8-[4-Chloro-N-(2.6-dimethylphenyl)-benzamido]-caprylic acid methyl ester, 2.2 g (55 mmol) of sodium hydroxide, 100 cc. of methanol and 5 cc. of water. Reaction time: 20 hours, reaction temperature: 25° C. The crude product is further purified chromatographically on silicic acid gel using chloroform as eluant.

Yield: 2.2 g (14% of the theoretical) of a colourless oil.
IR (film): 1735, 1714, 1645, 1618 cm$^{-1}$.
MS (m/e): 401 (15%), 280 (18%), 259 (100%), 139 (99%), 125 (30%), 120 (17%).

EXAMPLE 11

8-[2-Chloro-N-(3-chlorophenyl)-benzamido]-caprylic acid $R^1$=2-Chlorophenyl, $R^2$=3-Chlorophenyl, n=7, $R^3$=H (a) 8-(3-Chlorophenylamino)-caprylic acid methyl ester As described in example 3(a), the reaction is carried out with 6.4 g (50 mmol) of 3-chloroaniline, 5 g (50 mmol) of triethylamine, 13 g (55 mmol) of 8-bromocaprylic acid methyl ester and 40 cc. of cyclohexane. Reaction time: 6 hours, reaction temperature: 80° C.

Yield: 3.7 g (26% of the theoretical). Fp. 47°-49° C. (from ethanol).
IR (in KBr): 3400 and 1732 cm$^{-1}$.
MS (m/e): 283 (19%), 252 (5%), 140 (100%), 127 (8%).

(b) 8-[2-Chloro-N-(3-chlorophenyl)-benzamido]-caprylic acid methyl ester

As described in example 3(b), the reaction is carried out with 10 g (35 mmol) of 8-(3-chlorophenylamino)-caprylic acid methyl ester, 6.2 g (35 mmol) of 2-chlorobenzoic acid chloride, 3.9 g (39 mmol) of triethylamine and 100 cc. of ether. Reaction time: 24 hours, reaction temperature: 25° C. The crude product is further purified chromatographically on silicic acid gel using chloroform as eluant.

Yield: 11.4 g (77% of the theoretical) of a colourless oil.
IR (film): 1740 and 1660 cm$^{-1}$.
MS (m/e): 421 (5%), 390 (3%), 348 (2%), 265 (31%), 230 (5%), 139 (100%), 111 (13%).

(c) 8-[2-Chloro-N-(3-chlorophenyl)-benzamido]-caprylic acid

As described in example 1(b), the reaction is carried out with 3.8 g (9 mmol) of 8-[2-chloro-N-(3-chlorophenyl)-benzamido]-caprylic acid methyl ester, 0.48 g (12 mmol) of sodium hydroxide and 50 cc. of methanol. Reaction time: 24 hours, reaction temperature: 25° C. The crude product is purified chromatographically on silicic acid gel using chloroform as eluant.

Yield: 1 g (27% of the theoretical) of a colourless oil.
IR (film): 1710 and 1655 cm$^{-1}$.
MS (m/e): 407 (10%), 265 (31%), 139 (100%), 111 (10%).

EXAMPLE 12

8-{3.4.5-Trimethoxy-N-[3-(trifluoromethyl)-phenyl]-benzamido}-caprylic acid $R^1$=3.4.5-Trimethoxyphenyl,
$R^2$=3-(Trifluoromethyl)-phenyl, n=7, $R^3$=H (a) 8-[3-(Trifluoromethyl)-phenylamino]-caprylic acid methyl ester As described in example 3(a), the reaction is carried out with 16.1 g (0.1 mol) of 3-(trifluoromethyl)-aniline, 10.1 g (0.1 mol) of triethylamine, 23.7 g (0.1 mol) of 8-bromocaprylic acid methyl ester and 80 cc. of cyclohexane. Reaction time: 6 hours, reaction temperature: 80° C.

Yield: 8 g (25% of the theoretical). Fp. 47°-48° C. (from ethanol).
IR (in KBr): 3400 and 1740 cm$^{-1}$.
MS (m/e): 317 (18%), 286 (5%), 174 (100%), 161 (10%), 145 (2%).

(b) 8-{3.4.5-Trimethoxy-N-[3-(trifluoromethyl)-phenyl]-benzamido}-caprylic acid methyl ester As described in example 3(b), the reaction is carried out with 6.3 g (20 mmol) of 8-[3-(trifluoromethyl)-phenylamino]-caprylic acid methyl ester, 6.9 g (30 mmol) of 3.4.5-trimethoxybenzoic acid chloride, 2.5 g (25 mmol) of triethylamine and 150 cc. of ether. Reaction time: 24 hours, reaction temperature: 25° C. The crude product is used in the next reaction step without further purification.

Yield: 8.6 g (84% of the theoretical) of a colourless oil.

(c) 8-{3.4.5-Trimethoxy-N-[3-(trifluoromethyl)-phenyl]-benzamido}-caprylic acid

As described in example 1(b), the reaction is carried out with 8.6 g (16.8 mmol) of 8-{3.4.5-trimethoxy-N-[3-(trifluoromethyl)-phenyl]-benzamido}-caprylic acid methyl ester, 0.96 g (24 mmol) of sodium hydroxide and 100 cc. of methanol. Reaction time: 24 hours, reaction temperature: 25° C. The crude product is further purified chromatographically on silicic acid gel using chloroform as eluant.

Yield: 0.9 g (11% of the theoretical) of a colourless oil.
IR (film): 1715 and 1650 cm$^{-1}$.
MS (m/e): 497 (12%), 355 (6%), 195 (100%), 167 (3%).

EXAMPLE 13

8-[4-Chloro-N-(4-hydroxyphenyl)-benzamido]-caprylic acid $R^1$=4-Chlorophenyl, $R^2$=4-Hydroxyphenyl, n=7, $R^3$=H (a) 8-(4-Benzyloxyphenylamino)-caprylic acid methyl ester As described in example 3(a), the reaction is carried out with 22 g (0.11 mol) of 4-benzyloxyaniline, 12.1 g (0.12 mol) of triethylamine, 26.1 g (0.11 mol) of 8- bromocaprylic acid methyl ester and 80 cc. of cyclohexane. Reaction time: 6 hours, reaction temperature: 80° C. The reaction product is further purified chromatographically on silicic acid gel using chloroform as eluant.

Yield: 8.3 g (21% of the theoretical), Fp. 61°–62° C. (from ethanol).

IR (in KBr): 3400 and 1736 cm$^{-1}$.

MS (m/e): 355 (22%), 324 (5%), 264 (100%), 122 (11%), 108 (7%), 91 (14%), 55 (8%).

(b)

8-[4-Chloro-N-(4-benzyloxyphenyl)-benzamido]-caprylic acid methyl ether

As described in example 3(b), the reaction is carried out with 5.5 g (15.5 mmol) of 8-(4-benzyloxyphenylamino)-caprylic acid methyl ester, 2.7 g (15.5 mmol) of 4-chlorobenzoic acid chloride, 1.8 g (18 mmol) of triethylamine and 150 cc. ether. Reaction time: 24 hours, reaction temperature: 25° C. The crude product is used in the next reaction step without further purification.

Yield: 7.4 g (95% of the theoretical) of a colourless oil.

(c)

8-[4-Chloro-N-(4-benzyloxyphenyl)-benzamido]caprylic acid

As described in example 1(b), the reaction is carried out with 7.4 g (15 mmol) of 8-[4-chloro-N-(4-benzyloxyphenyl)-benzamido]-caprylic acid methyl ester, 1 g (23 mmol) of sodium hydroxide and 200 cc. of methanol. Reaction time: 48 hours, reaction temperature: 25° C. The crude product is used in the next reaction step without further purification.

Yield: 6 g (83% of the theoretical) of a yellow oil.

(d)

8-[4-Chloro-N-(4-hydroxyphenyl)-benzamido]-caprylic acid ethyl ester

Hydrogen is bubbled into a mixture of 6 g (12.5 mmol) of 8-[4-chloro-N-(4-benzyloxyphenyl)-benzamido]-caprylic acid, 250 cc of ethanol and 1.2 g of palladium-activated carbon-hydrogenation catalyst (containing 10 weight % of Pd) at 25° C. and normal pressure with vivid stirring. After 2 hours and the uptake of 280 cc. (12.2 mmol) of hydrogen, the reaction is stopped. The catalyst is filtered off and the ethanol is distilled off under reduced pressure. The residue is dissolved in 150 cc. of ether, the ethereal solution is mixed with dilute sodium carbonate solution, dried over sodium sulphate and the solvent is destilled off. The residue is rechrystallized from a mixture of ether and n-hexane.

Yield: 3.5 g (67% of the theoretical). Fp. 89°–90° C. (from ether/n-hexane).

IR (in KBr): 3200, 1735 and 1610 cm$^{-1}$.

MS (m/e): 417 (31%), 372 (8%), 247 (32%), 139 (100%), 125 (9%), 122 (8%), 111 (9%), 105 (19%).

(e)

8-[4-Chloro-N-(4-hydroxyphenyl)-benzamido]-caprylic acid

As described in example 1(b), the reaction is carried out with 3.5 g (8.4 mmol) of 8-[4-chloro-N-(4-hydroxyphenyl)-benzamido]-caprylic acid ethyl ester, 0.7 g (17.5 mmol) of sodium hydroxide and 100 cc. of ethanol. Reaction time: 24 hours, reaction temperature: 25° C.

Yield: 1.8 g (55% of the theoretical). Fp. 138°–139° C. (from ethanol).

IR (in KBr): 3400, 1715 and 1620 cm$^{-1}$.

MS(m/e): 389 (28%), 355 (10%), 247 (27%), 139 (100%), 122 (25%), 111 (12%), 105 (35%).

EXAMPLE 14

8-[3-Hydroxy-N-(4-hydroxyphenyl)-benzamido]-caprylic acid $R^1$=3-Hydroxyphenyl, $R^2$=4Hydroxyphenyl, n=7, $R^3$=H (a)

8-[3-Benzyloxy-N-(4-benzyloxyphenyl)-benzamido]-caprylic acid methyl ester

As described in example 3(b), the reaction is carried out with 4.7 g (13 mmol) of 8-(4-benzyloxyphenylamino)-caprylic acid methyl ester, 3.3 (13 mmol) of 3-benzyloxy- benzoic acid choride, 1.5 g (15 mmol) of triethylamine and 100 cc. of ether. Reaction time: 24 hours, reaction temperature: 25° C. The crude product is used in the next reaction step without further purification.

Yield: 7 g (93% of the theoretical) of a yellow oil.

(b)

8-[3-Hydroxy-N-(4-hydroxyphenyl)-benzamido]-caprylic acid methyl ester

Hydrogen is bubbled into a mixture of 7 g (12 mmol) of 8-[3-benzyloxy-N-(4-benzyloxyphenyl)-benzamido]-caprylic acid methyl ester, 200 cc. of methanol and 0.7 g of a palladium-activated carbon-hydrogenation catalyst (containing 10 weight % of Pd) at 25° C. and normal pressure with vivid stirring. After 1 hour and the uptake of 560 cc. (24 mmol) of hydrogen, the reaction is stopped. The catalyst is filtered off. Methanol is distilled off under reduced pressure and the residue is purified chromatographically on silicic acid gel using a mixture of ethyl acetate and n-hexane as eluant.

Yield: 2.6 g (57% of the theoretical). Fp. 132°–133° C. (from ethyl acetate/n-hexane).

IR (in KBr): 3410, 1745 and 1580 cm$^{-1}$.

MS (m/e): 385 (35%), 354 (5%), 264 (8%), 242 (13%), 229 (26%), 135 (5%), 121 (100%), 93 (14%).

(c)

8-[3-Hydroxy-N-(4-hydroxyphenyl)-benzamido]-caprylic acid

As described in example 1(b), the reaction is carried out with 1.3 g (3.4 mmol) of 8-[3-hydroxy-N-(4-hydroxyphenyl)-benzamido]-caprylic acid methyl ester, 0.2 g (5 mmol) of sodium hydroxide and 50 cc. of methanol. Reaction time: 4 days, reaction temperature: 25° C.

Yield: 0.92 g (74% of the theoretical). Fp. 133° C. (from ethanol).

IR (in KBr): 3400, 1700, 1605 and 1570 cm$^{-1}$. MS (m/e): 371 (30%), 250 (8%), 242 (12%), 229 (23), 135 (4%), 121 (100% ), 93 (16%).

EXAMPLE 15

8-[4-Chloro-N-(4-chlorophenyl)-benzamido]-caprylic acid sodium salt $R^1$=4-Chlorophenyl, $R^2$=4-Chlorophenyl, n=7, $R^3$=Na 2.6 g (4.9 mmol) of 8-[4-chloro-N-(4-chlorophenyl)-benzamido]-caprylic acid are dissolved in 50 cc. of methanol. A solution of 0.25 g (4.6 mmol) of sodium methylate in 50 cc. of methanol are added thereto and the mixture is stirred for 15 minutes at 25° C. The sodium salt is precipitated by the addition of ether, is filtered off with suction, is dried and powdered.

Yield: 1.3 g (62% of the theoretical).
IR (in KBr): 1655 cm$^{-1}$.

EXAMPLE 16

8-(N-Phenyl-benzamido)-caprylic acid sodium salt $R^1$=Phenyl, $R^2$=Phenyl, n=7, $R^3$=Na 8-(N-phenyl-benzamido)-caprylic acid is dissolved in ethanol and neutralized with an ethanolic soda lye. The solution is evaporated in a vacuum and the solid residue is powdered.
IR (in KBr): 1648 and 1568 cm$^{-1}$.

EXAMPLES 17 to 28

The examples have been carried out as described in example 16. The corresponding IR-dates are given in the following table I.

N—Benzoyl-ω-anilino alkanoic carboxylic acid sodium salts of formula I ($R^3$ = Na) from the corresponding acids of formula I ($R^3$ H)

$$R^1-\underset{\underset{R^2}{|}}{\overset{\overset{O}{\|}}{C}}-N-(CH_2)_n-\overset{\overset{O}{\|}}{C}-OR^3 \qquad I$$

| Example No. | $R^1$ | $R^2$ | n | $R^3$ | IR-dates (in KBr) cm$^{-1}$ |
|---|---|---|---|---|---|
| 17 | CH₃—O—C₆H₄— | CH₃O—C₆H₄— | 7 | Na | 1645,1568 |
| 18 | Cl—C₆H₄— | CH₃O—C₆H₄— | 7 | Na | 1642,1568 |
| 19 | Cl—C₆H₄— | CH₃O—C₆H₄— | 8 | Na | 1645,1568 |
| 20 | Cl—C₆H₄— | CH₃O—C₆H₄— | 10 | Na | 1650,1570 |
| 21 | F—C₆H₄— | CH₃O—C₆H₄— | 7 | Na | 1645,1568 |
| 22 | 3-CF₃—C₆H₄— | CH₃O—C₆H₄— | 7 | Na | 1645,1570 |
| 23 | 3,4-Cl,Cl—C₆H₃— | CH₃O—C₆H₄— | 7 | Na | 1655,1565 |
| 24 | Cl—C₆H₄— | 3,4-(CH₃)₂—C₆H₃— | 7 | Na | 1645,1570 |
| 25 | 3-Cl—C₆H₄— | 3-Cl—C₆H₄— | 7 | Na | 1660,1570 |
| 26 | 3,4,5-(CH₃O)₃—C₆H₂— | 3-CF₃—C₆H₄— | 7 | Na | 1655,1570 |
| 27 | Cl—C₆H₄— | HO—C₆H₄— | 7 | Na | 3400, 1625, 1565 |
| 28 | 3-HO—C₆H₄— | HO—C₆H₄— | 7 | Na | 3400, 1620, 1580 |

EXAMPLE 29

8-(N-Phenyl-benzamido)-caprylic acid ethyl ester $R^1$=Phenyl, $R^2$=Phenyl, n=7, $R^3$=—CH₂—CH₃

0.33 g (2.9 mmol) of ethyl bromide are added to a mixture of 1 g (2.9 mmol) of 8-(N-phenyl-benzamido)-caprylic acid, 20 cc. of dimethylformamide and 0.48 g (5.8 mmol) NaHCO₃. The mixture is stirred for 3 days and 25° C. Thereafter 100 cc. of water are added and the mixture is extracted with ethyl acetate. The organic layer is washed with water, dried over Na₂SO₄ and the solvent is distilled off in a vacuum. The residue is purified chromatographically on silicic acid gel using chloroform as eluant.

Yield: 0.33 g (31% of the theoretical) of a yellow oil.
IR (film): 1738 and 1645 cm$^{-1}$.
MS (m/e): 367 (25%), 322 (11%), 197 (42%), 105 (100%), 77 (16%).

EXAMPLE 30

8-[4-Chloro-N-(4-methoxyphenyl)-benzamido]-caprylic acid isopropyl ester $R^1$=4-Chlorophenyl, $R^2$=4-Methoxyphenyl, n=7, $R^3$=—CH(CH₃)₂

As described in example 29, the reaction is carried out with 3 g (7.5 mmol) of 8-[4-Chloro-N-(4-methoxyphenyl)-benzamido]-caprylic acid, 50 cc. of dimethylformamide, 1.26 g (15 mmol) NaHCO3 and 9.2 g (75 mmol) of 2-bromopropane.

Yield: 0.4 g (12% of the theoretical) of a colourless oil.

IR (film): 1730 and 1645 cm⁻¹.

MS (m/e): 445 (47%), 386 (15%), 261 (40%), 139 (100%), 125 (13%).

EXAMPLE 31

8-[4-Chloro-N-(4-methoxylphenyl)-benzamido]-caprylic acid heptyl ester

R¹=4-Chlorophenyl, R²=4-Methoxyphenyl, n=7, R³=—(CH2)6CH3

As described in example 29, the reaction is carried out with 3 g (7.5 mmol) of 8-[4-chloro-N-(4-methoxyphenyl)-benzamido]-caprylic acid, 50 cc. of dimethylformamide, 1.26 g (15 mmol) of NaHCO3 and 13.4 g (75 mmol) of 1-bromoheptane.

Yield: 0.8 g (22% of the theoretical) of a colourless oil.

IR (film): 1737 and 1647 cm⁻¹.

MS (m/e): 501 (83%), 386 (11%), 261 (43%), 139 (100%), 125 (12%).

EXAMPLE 32

8-[2.4-Dichloro-N-(4-methoxyphenyl)-benzamido]-caprylic acid benzyl ester

R¹=2.4-Dichlorophenyl, R²=4-Methoxyphenyl, n=7, R³=Benzyl

As described in example 29 the reaction is carried out with 2 g (4.6 mmol) of 8-[2.4-dichloro-N-(4-methoxyphenyl)-benzamido]-caprylic acid, 40 cc. of dimethylformamide, 0.77 g (9 mmol) of NaHCO3 and 7.8 g (46 mmol) of benzylbromide.

Yield: 0.9 g (37% of the theoretical) of a colourless oil.

IR (film): 1740 and 1655 cm⁻¹.

MS (m/e): 527 (63%), 420 (9%), 295 (54%), 173 (100%), 136 (15%), 91 (72%).

The following examples refer to mixtures of compounds of formula I with carrier and auxiliary agents usual in pharmacy which mixtures can be used as drugs.

EXAMPLE 33

Tablets

A mixture consisting of 50 g of the sodium salt of 8-[4-chloro-N-(4-chlorophenyl)-benzamido]-caprylic acid, 50 g of lactose, 15 g of corn starch, 2 g of cellulose powder and 2 g of magnesium stearate, pressed in usual manners to tablets such that each tablet contains 250 mg of active agent.

EXAMPLE 34

Dragees

As described in example 33, tablets are pressed and then are coated with a coating consisting of sugar, corn starch, talcum and tragant.

EXAMPLE 35

Ampoules 100 g of the sodium salt of 8-[4-chloro-N-(4-chlorophenyl)-benzamido]-caprylic acid are dissolved in a mixture of 9.5 liter of bedestilled water and 0.5 liter of ethylen glycol, filtered and filled into ampoules each containing 10 cc. of the solution under sterile conditions. The ampoules thereafter are closed by fusion.

In analogous manner there are produced tablets, dragees, and ampoules containing one or several active agents of formula I with the addition of an anticoagulating agent.

What we claim is:

1. N-Benzoyl-ω-anilinoalkane carboxylic acid of the general formula I

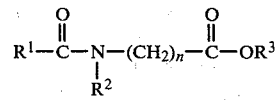

wherein n is a positive integer ranging from 7 to 10;

R¹ and R², which may be different from each other or identical, represent the unsubstituted phenyl group or the phenyl group substituted by 1 to 4 identical or different groups selected from the group of halogen, C₁₋₄-alkyl, C₁₋₄-alkoxy, C₁₋₄-alkylthio, halogeno-C₁₋₄-alkyl, hydroxy, phenoxy, benzyloxy, acyloxy or di-C₁₋₄-alkylamino, R³ is hydrogen, an alkali ion or a straight or branched saturated hydrocarbon group having 1 to 7 carbon atoms or the benzyl group.

2. N-Benzoyl-ω-anilino alkane carboxylic acids according to claim 1 and formula I wherein n is 7 or 8;

R¹ and R², which may be identical or different from each other, represent the unsubstituted phenyl or phenyl substituted by 1 to 3 Cl—, F—, CF3—, CH3—, HO— and/or CH3O— groups;

R³ is hydrogen, an alkali ion, preferably the sodium ion or a straight or branched saturated hydrocarbon group having from 1 to 7 carbon atoms.

3. 8-(N-Phenyl-benzamido)-caprylic acid and the pharmaceutically compatible salts and esters thereof according to claim 1.

4. 8-[4-Chloro-N-(4-chlorophenyl)-benzamido]-caprylic acid and the pharmaceutically compatible salts and esters thereof according to claim 1.

5. 8-[4-Methoxy-N-(4-methoxyphenyl)-benzamido]-caprylic acid and the pharmaceutically compatible salts and esters thereof according to claim 1.

6. 8-[4-Chloro-N-(4-methoxyphenyl)-benzamido]-caprylic acid and the pharmaceutically compatible salts and esters thereof according to claim 1.

7. 9-[4-Chloro-N-(4-methoxyphenyl)-benzamido]-pelargonic acid and the pharmaceutically compatible salts and esters thereof according to claim 1.

8. 11-[4-Chloro-N-(4-methoxyphenyl)-benzamido]-undecane acid and the pharmaceutically compatible salts and esters thereof according to claim 1.

9. 8-[4-Fluoro-N-(4-methoxyphenyl)-benzamido]-caprylic acid and the pharmaceutically compatible salts and esters thereof according to claim 1.

10. 8-[3-Trifluoromethyl-N-(4-methoxyphenyl)-benzamido]-caprylic acid and the pharmaceutically compatible salts and esters thereof according to claim 1.

11. 8-[2.4-Dichloro-N-(4-methoxyphenyl)-benzamido]-caprylic acid and the pharmaceutically compatible salts and esters thereof according to claim 1.

12. 8-[4-Chloro-N-(2.6-dimethylphenyl)-benzamido]-caprylic acid and the pharmaceutically compatible salts and esters thereof according to claim 1.

13. 8-[2-Chloro-N-(3-chlorophenyl)-benzamido]-caprylic acid and the pharmaceutically compatible salts and esters thereof according to claim 1.

14. 8-[3.4.5-Trimethoxy-N-]3-(trifluoromethyl)-phenyl[-benzamido]-caprylic acid and the pharmaceutically compatible salts and esters thereof according to claim 1.

15. 8-[4-Chloro-N-(4-hydroxyphenyl)-benzamido]-caprylic acid and the pharmaceutically compatible salts and esters thereof according to claim 1.

16. 8-[3-Hydroxy-N-(4-hydroxyphenyl)-benzamido]-caprylic acid and the pharmaceutically compatible salts and esters thereof according to claim 1.

17. N-Benzoyl-$\omega$-anilino alkane carboxylic acids according to claim 2 and formula I wherein n is 7, $R^1$ is unsubstituted phenyl or phenyl substituted by halogen, and $R^2$ is unsubstituted phenyl or phenyl substituted in the para position by a chlorine atom, a hydroxy group or a methoxy group.

18. N-Benzoyl-$\omega$-anilino alkane carboxylic acids according to claim 17 wherein $R^1$ is substituted by up to 2 halogen atoms selected from the group consisting of fluorine or chlorine atoms.

* * * * *